(12) United States Patent  
Ahmed et al.

(10) Patent No.: US 8,354,547 B2  
(45) Date of Patent: Jan. 15, 2013

(54) 4β-AMINO PODOPHYLLOTOXIN CONGENERS AS ANTI TUMOUR ANTIBIOTICS A PROCESS FOR THE PREPARATION THEREOF

(75) Inventors: Kamal Ahmed, Andhra Pradesh (IN); Ashwini Kumar Banala, Andhra Pradesh (IN); Suresh Paidakula, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/127,572

(22) PCT Filed: Mar. 24, 2009

(86) PCT No.: PCT/IN2009/000194  
§ 371 (c)(1), (2), (4) Date: May 4, 2011

(87) PCT Pub. No.: WO2010/052733  
PCT Pub. Date: May 14, 2010

(65) Prior Publication Data  
US 2011/0213165 A1    Sep. 1, 2011

(30) Foreign Application Priority Data  
Nov. 7, 2008    (IN) .............................. 2535/DEL/2008

(51) Int. Cl.  
*C07D 307/77*    (2006.01)
(52) U.S. Cl. ...................................................... 549/298
(58) Field of Classification Search .................... 549/298  
See application file for complete search history.

(56) References Cited

U.S. PATENT DOCUMENTS 5,132,322 A * 7/1992 Lee et al. ...................... 514/468

(Continued)

FOREIGN PATENT DOCUMENTS

WO    03/082876 A1    10/2003

(Continued)

OTHER PUBLICATIONS

Kamal et al. Tetrahedron Letters, 2003, 44, 8457-8459.*

(Continued)

*Primary Examiner* — Nizal Chandrakumar  
(74) *Attorney, Agent, or Firm* — Fitzpatrick, Cella, Harper & Scinto

(57) ABSTRACT

The present invention provides novel β-amino podophyllotoxin congeners of general formula (A); $R=CH_3$, or H; $R_1$=(a) or (b) or (c) or (d) or (e) or (f). The present invention also provides a process for the preparation of 4β-amino podophyllotoxin congeners useful as antitumour agents.

6 Claims, 5 Drawing Sheets (A)

(a)

(b)

(c)

(d)

(e)

(f)

U.S. PATENT DOCUMENTS 7,087,641 B2 * 8/2006 Kamal et al. .................. 514/463

FOREIGN PATENT DOCUMENTS

WO 2004/033423 A2 4/2004

OTHER PUBLICATIONS

Chen, Y. et al., "Anticancer drugs part III: New spin labelled derivatives of podophyllotoxin," Curr. Sci., vol. 59, pp. 517-518 (1990).

Saito, H. et al., "Studies on Lignan Lactone Antitumor Agents. I. Synthesis of Aminoglycosidic Lignan Variants Related to Podophyllotoxin," Chem. Pharm. Bull., vol. 34, No. 9, pp. 3733-3740 (1986).

Chen, Y. Z. et al., "Anticancer Drugs II. Synthesis and Biological Evaluation of Spin Labeled Derivatives of Podophyllotoxin," Life Sciences, vol. 45, pp. 2569-2575 (1989).

Lee, K. H. et al., "Antitumor Agents, 107. New Cytotoxic 4-Alkylamino Analogues of 4'-Demethyl-Epipodophyllotoxin As Inhibitors of Human DNA Topoisomerase II," Journal Nat. Prod., vol. 52, No. 3, pp. 606-613 (1989).

Lee, K. H. et al., "Antitumor Agents. III. New 4-Hydroxylated and 4-Halogenated Anilino Derivatives of 4'Demethylepipodophyllotoxin as Potent Inhibitors of Human DNA Topoisomerase II," J. Med. Chem., vol. 33, pp. 1364-1368 (1990).

Kamal, A., et al., "Synthesis and biological evaluation of new 4β-anilino- and 4β-imido-substituted podophyllotoxin congeners," Bioorg. & Med. Chem., vol. 13, pp. 6218-6225 (2005).

Kamal, A. et al., "Synthesis of 4β-amido and 4β-sulphonamido Analogues of Podophyllotoxin as Potential Antitumor Agents," Bioorg. & Med. Chem., vol. 11, pp. 5135-5142 (2003).

Kamal, A, et al., "A one-pot, efficient and facile synthesis of 4β-arylaminopodophyllotoxins: synthesis of NPF and GL-331 as DNA topoisomerase II inhibitors," Tetrahedron Lett., vol .44, pp. 8457-8459 (2003).

Kamal, A. et al., "Design, synthesis, biological evaluation and QSAR studies of novel bisepipodophyllotoxins as cytotoxic agents," Bioorganic & Medicinal Chemistry, vol. 12, pp. 4197-4209 (Jun. 2004).

* cited by examiner

Podophyllotoxin

R = CH₃   Etoposide

R =  Teniposide

Fig-2: Topoisomerase-I assay for compounds 3d, 4d, 3c and 4c
Lane1-Supercoiled DNA, Lane2-Relaxed DNA, Lane3-Supercoiled+Topo-I
Lane4-Supercoiled+Topo-1+Compto (100μM)
Lane5-Supercoiled+Topo-1+Compound3d (100μM)
Lane6-Supercoiled+Topo-1+ Compound4d (100μM)
Lane7-Supercoiled+Topo-1+ Compound3c (100μM)
Lane8-Supercoiled+Topo-1+ Compound4c (100μM)

Fig-3: Topoisomerase-II Inhibition for compounds 3d, 4d and 4c
Lane1-Supercoiled DNA+Enzyme Lane2-Supercoiled DNA, Lane3-Linear DNA
Lane4-Supercoiled+Topo-1+Compto (100μM)
Lane5-Compound3d (100μM)
Lane6-Compound4d (100μM)
Lane7- Compound4c (100μM)
Lane8-VP-16 (100μM)

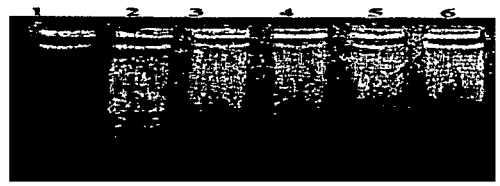
Fig-4: DNA fragmentation assay for compound 3d
Lane1- -ve Control
Lane2-Camtothecin (5μM)
Lane3-Compound3d (0.5μM)
Lane4-Compound3d (1μM)
Lane5- Compound3d (5μM)
Lane6-Compound3d (10μM)

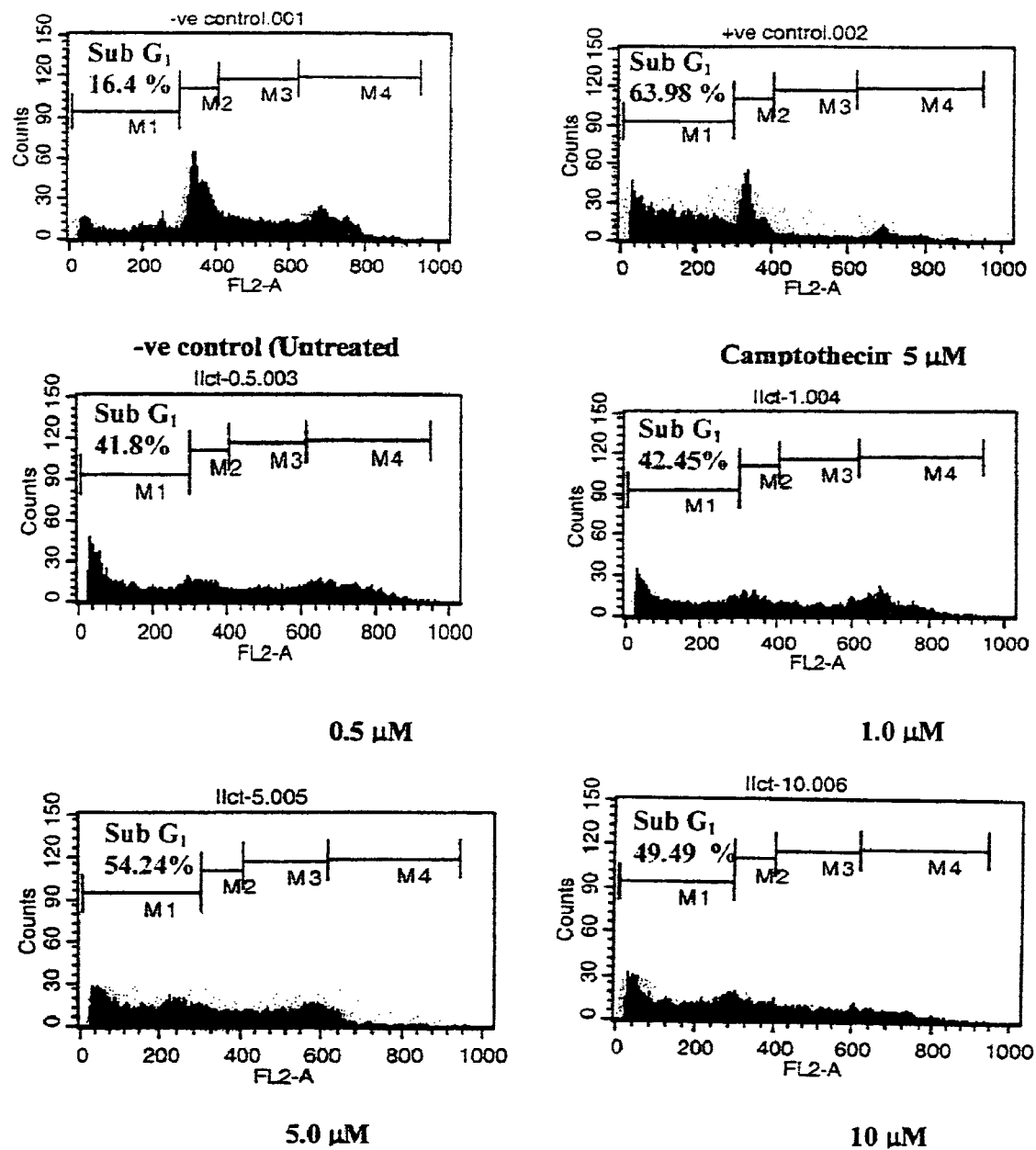
Fig-5: DNA cell cycle analysis for compound 3d

4β-AMINO PODOPHYLLOTOXIN CONGENERS AS ANTI TUMOUR ANTIBIOTICS A PROCESS FOR THE PREPARATION THEREOF

FIELD OF THE INVENTION

The present invention relates to novel 4β-amino podophyllotoxin congeners as antitumour antibiotics. More particularly, the present invention relates to novel β-amino podophyllotoxin congeners of general formula A

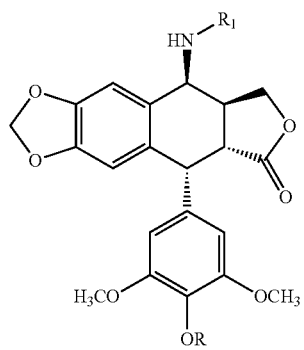

R = CH₃, or H

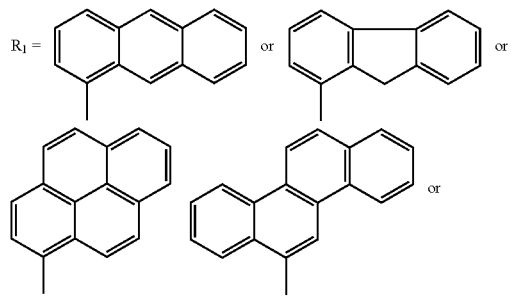

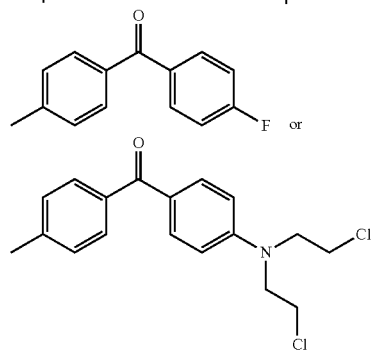

The present invention also relates to a process for the preparation of 40-amino podophyllotoxin congeners.

BACKGROUND OF THE INVENTION

Etoposide and teniposide are semi-synthetic podophyllotoxin derivatives that are in clinical usage as an anticancer drugs FIG. 1 (Chen. Y. Z.; Wang. Y. G.; Tian, X.; Li, J. X. *Curr. Sci* 1990, 59, 517.; Wang, J. Z.; Tian, X.; Tsumura, H.; Shimura, K.; Ito, H. *Anti-cancer Drug Design,* 1993, 8, 193). It is believed that analogues of 4'-demethyl epipodophyllotoxin exert their antitumour activity through stabilization of a cleavable complex between DNA and type II DNA topoisomerase, this leads ultimately to inhibition of DNA catenation activity and produces single and double strand breaks (Satio, H.; Yoshikawa, H.; Nishimura, Y.; Kondo, S.; Takeuchi, T.; Umezawa, H. *Chem. Pharm. Bull.* 1986, 34, 3733.; Chen, Y. Z.; Wang, Y. G.; Li, J. X.; Tian, X.; Jia. Z. P.; Zhang, Z. Y. *Life Sci.* 1989, 45, 2569) A number of studies have been carried out on the structural modification of glycoside by amino substituents that has improved the inhibitory activity on human DNA topoisomerase II as well as stronger activity in causing cellular protein length DNA breakage (Lee, K. H.; Imakura, Y.; Haruna, M.; Beers, S. A.; Thurston, L. S.; Dai, H. J.; Chen, C. H.; Liu, S. Y.; Cheng, Y. C. *J Nat. Prod.* 1989, 52, 606.; Liu, S. Y.; Hawang, B. D.; Haruna, M.; Imakura, Y.; Lee, K. H.; Cheng, Y. C. *Mol. Pharmcol.* 1989; 36, 8.; Lee, K, H.; Beers, S. A.; Mori, M.; Wang, Z. Q.; Kuo, Y. H.; Li, L.; Liu, S. Y.; Cheng, Y. C.; *J. Med. Chem.* 1990, 33, 1364.; Kamal, A.; Gayatri, N. L.; Reddy, D. R; Reddy, P. S. M. M.; Arifuddin, M.; Dastidar, S. G.; Kondapi, M. A.; Rajkumar M. *Bioorg. Med. Chem.* 2005, 13, 6218; Kamal, A.; Kumar, B. A.; Arifuddin, M.; Dastidar, S. G. *Bioorg. Med. Chem.* 2003, 11, 5135). In this context a large number of 4β-amino derivatives of podophyllotoxin and 4'-O-demethyl epipodophyllotoxin based compounds have been synthesized and investigated for their antitumour activity.

OBJECTIVE OF THE INVENTION

The main object of the invention is to provide the novel 4β-amino podophyllotoxin congeners as useful antitumour antibiotics.

Another object of the present invention is to provide a process for the synthesis of these new 4β-amino derivatives of podophyllotoxin as useful anticancer or antitumour agents.

Another object of the present invention is to provide new and stereoselective compounds based on the podophyllotoxin and 4'-O-demethylepipodophyllotoxin in good yields.

SUMMARY OF THE INVENTION

Accordingly the present provides novel 4β-amino podophyllotoxin congeners of general formula A as antitumour antibiotics.

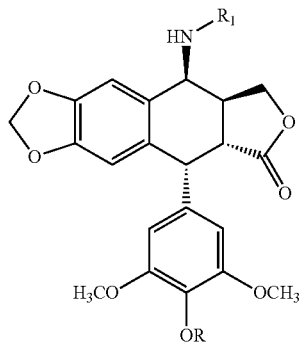

R = CH₃, or H

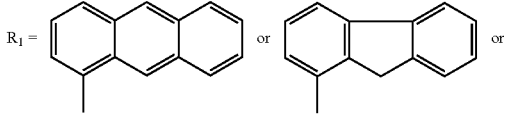

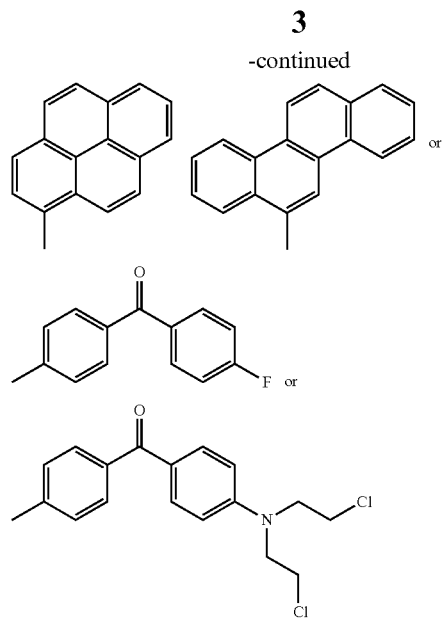
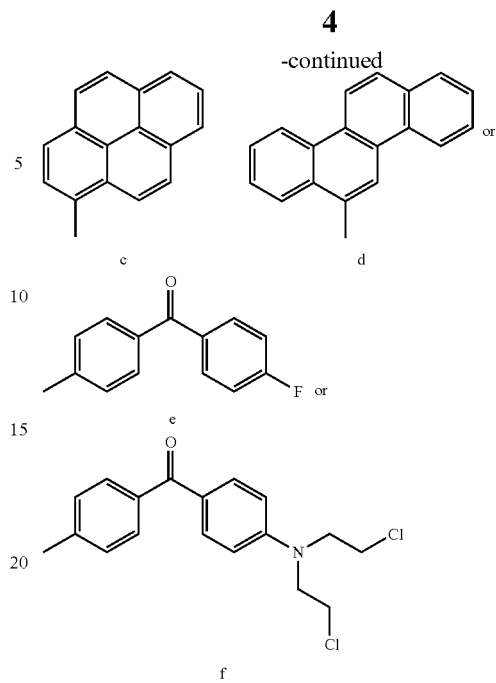

In an embodiment of the present invention the novel 4β-amino podophyllotoxin congeners formula A is represented by the following compounds of formula 3a-f and 4a-f

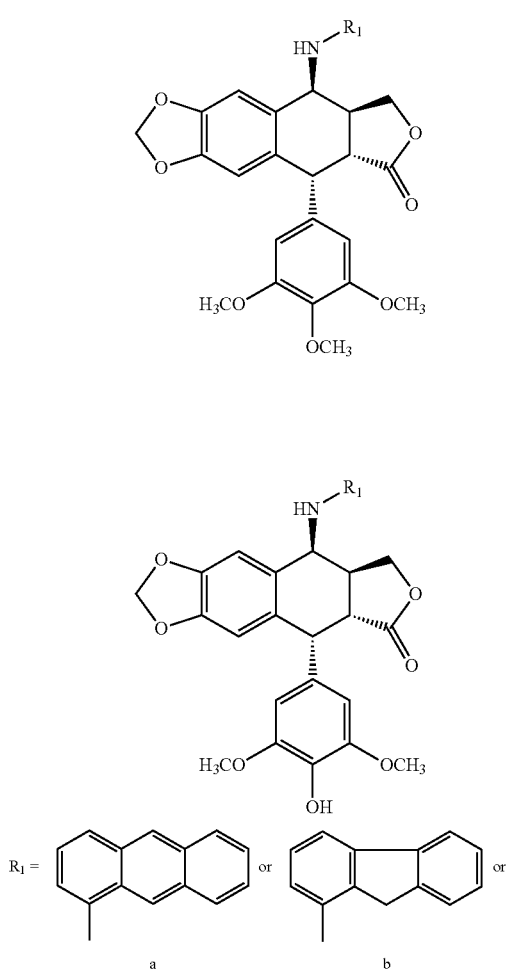

In yet another embodiment the novel 4β-amino podophyllotoxin congeners is represented by the following compounds:

4β-(1"-Anthrylamino)-4-desoxypodophyllotoxin (3a);
4β-(1"-Fluorenylamino)-4-desoxypodophyllotoxin (3b);
4β-(1"-Pyrenylamino)-4-desoxypodophyllotoxin (3c);
4β-(6"-Chrycenylamino)-4-desoxypodophyllotoxin (3d);
4β-[4"-(4"-Fluorobenzoyl)anilino]-4-desoxypodophyllotoxin (3e);
4β-(4"-{4"-[Di(2"-chloroethyl)amino]benzoyl}anilino)-4-desoxypodophyllotoxin (3f);
4'-O-Demethyl-4β-(1"-anthrylamino)-4-desoxypodophyllotoxin (4a);
4'-O-Demethyl-4β-(1"-fluorenylamino)-4-desoxypodophyllotoxin (4b);
4'-O-Demethyl-4β-(1"-pyrenylamino)-4-desoxypodophyllotoxin (4c);
4'-O-Demethyl-4β-(1"-chrycenylamino)-4-desoxypodophyllotoxin (4d);
4'-O-Demethyl-4β-[4"-(4"-fluorobenzoyl)anilino]-4-desoxypodophyllotoxin (4e) and
4'-O-Demethyl-4β-(4"-{4-[di(2"-chloroethyl)amino]benzoyl}anilino)-4-desoxy podophyllotoxin (4f).

The present invention further provides a process for the preparation of 4(3-amino podophyllotoxin congeners of general formula A as antitumour antibiotics

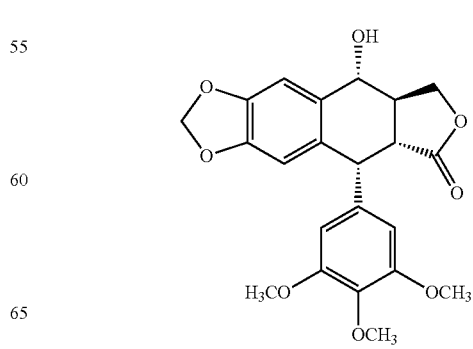

-continued

Formula A

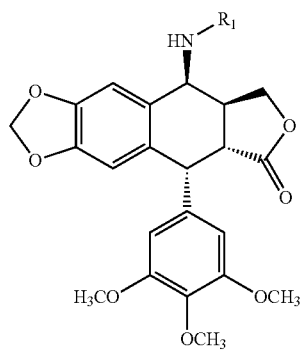

R = CH₃, or H

R₁ = 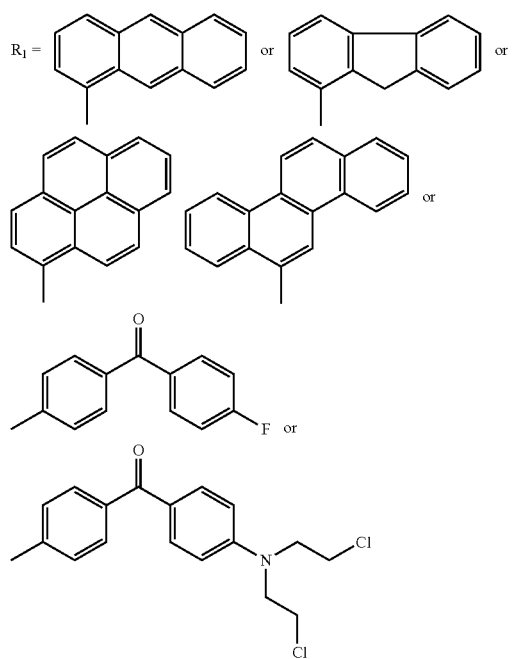

and the said process comprising the steps of:

a) reacting podophyllotoxin of formula 1 with sodium iodide in dry acetonitrile, under stirring, followed by adding drop wise BF₃OEt₂ at a temperature of 0-1° C. and continuing the stirring for a period of 0.3-0.6 hrs, at a temperature of 20-30° C., followed by evaporation in vacuo to obtain the compound of formula 2a, 2a

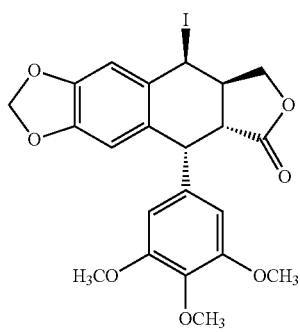

OR reacting podophyllotoxin of formula 1 with sodium iodide in dry dichloromethane, under stirring, followed, by adding drop wise BF₃OEt₂ at a temperature of 0-1° C. and continuing the stirring for a period of 5-6 hrs, at a temperature of 20-30° C., followed by evaporation in vacuo to obtain the compound of formula 2b, 2b

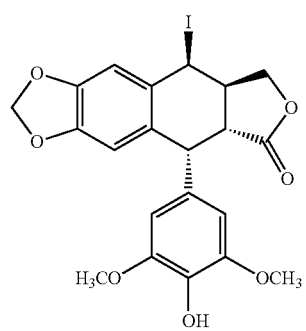

b) reacting the above said compound of formula 2a or 2b with anhydrous barium carbonate and the reagent selected from the group consisting of 1-anthraceneamine, 1-fluorenylamine, 4β-(1"-pyrenylamino)-4-deoxypodophyllotoxin, 1-pyrenylamine, 6-chrycenylamine, 4-amino-4'-fluorobenzophenone and 4-amino-4'-[di(2-chloroethyl)amino]benzophenone in dry tetrahydrofuran (THF), under notrogenand stirring for a period of 7-9 hrs, at a temperature of 20-30° C., followed by filtration, washing with water and drying by known method to obtain the desired corresponding, compounds of formula 3a-f and 4a-f 3a-f

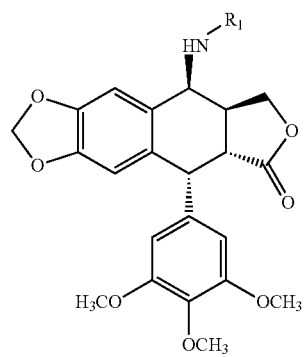

4a-f

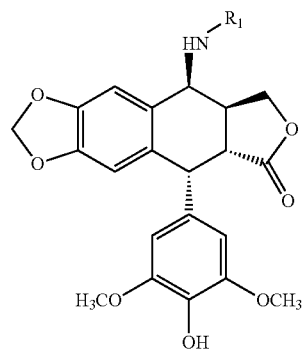

-continued

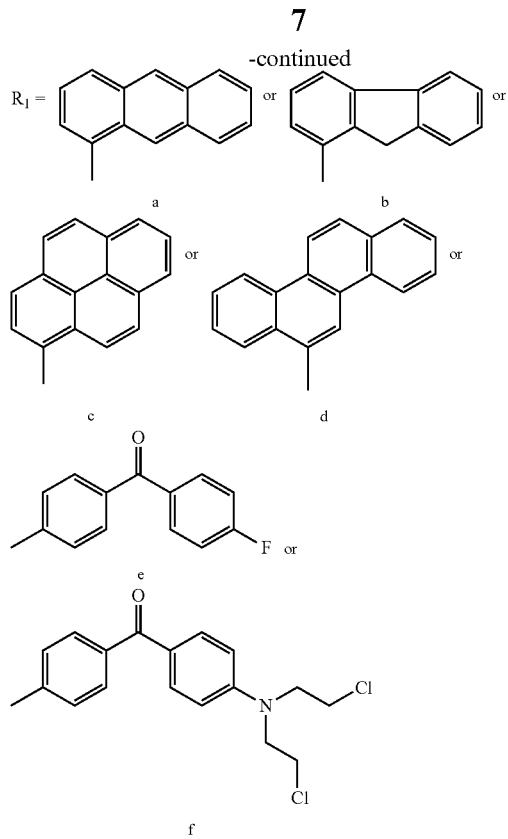

In still another embodiment the novel 4β-amino podophyllotoxin congeners obtained are useful as antitumour antibiotics.

BRIEF DESCRIPTION OF THE DRAWINGS

FIG. 2 shows a Topoisomerase-I assay for compounds 3d, 4d, 3c and 4c;

FIG. 3 shows a Topoisomerase-II inhibition for compounds 3d, 4d and 4c;

FIG. 4 shows a DNA fragmentation assay for compound 3d; and

FIG. 5 shows a DNA cell cycle analysis for compound 3d.

DETAILED DESCRIPTION

Figure 1:
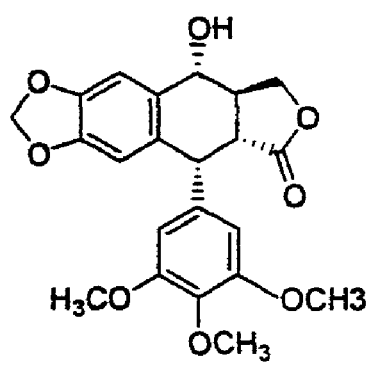
FIG. 1 shows the structure of podophyllotoxin and semi-synthetic podophyllotoxin derivatives Etoposide and teniposide.
Figure 1:
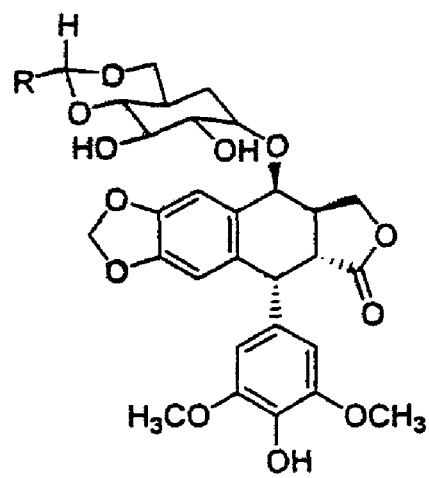
Figure 1:
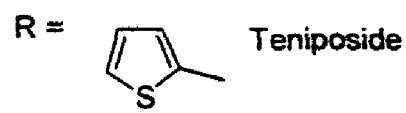
Figure 1:
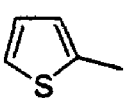

The process for the synthesis of new podophyllotoxin analogues as anticancer agents produces the novel and stereoselective derivatives of the podophyllotoxin in good yields, where in the key step for the synthesis of these analogues is by direct nucleophilic substitution of C-4β-iodo intermediates. The 4β-iodopodophyllotoxin, which has been reacted with substituted or unsubstituted polyarylamines in a stereo-selective manner to afford the 4β-polyarylamino derivatives of podophyllotoxin.

These 4-iodopodophyllotoxin intermediates have been prepared by the iodination of the related podophyllotoxin compounds as described in the literature (Kamal, A.; Kumar, B. A.; Arifuddin, M. *Tetrahedron Lett.* 2003, 44, 8457.).

In an embodiment of the present invention, the naturally occurring podophyllotoxin lignan was isolated from *Podophyllunt peltatum linnaeus*.

In another embodiment of the present invention the synthesis of 4β-intermediates have been carried out from iodination of podophyllotoxin.

In yet another embodiment of the present invention 1-2 eq. of different unsubstituted and substituted Polyarylamine compounds have been used.

In still another embodiment of the present invention a variety of solvents were used for the nucleophilic substitution step, such as dichloromethane, chloroform and tetrahydrofuran.

In still another embodiment of the present invention bases like $K_2CO_3$, $Et_3N$ were used.

In still another embodiment of the present invention the purification of these analogues was done by column chromatography employing ethylacetate/hexane as eluent.

Thus the present invention provides new class of podophyllotoxin analogues, which were synthesized in a stereoselective manner.

A program was initiated in the laboratory for the design and synthesis of new 4β-aryl amino substituted podophyllotoxin congeners with enhanced antitumour activity and/or activity against etoposide resistant tumor cell lines. In these efforts new 4β-polyarylamino derivatives of podophyllotoxin have been synthesized and evaluated for their cytotoxicity and anticancer potency compared to adiramycin. The synthesis of these compounds has been carried out as described in the Scheme 1 using podophyllotoxin obtained from the resin.

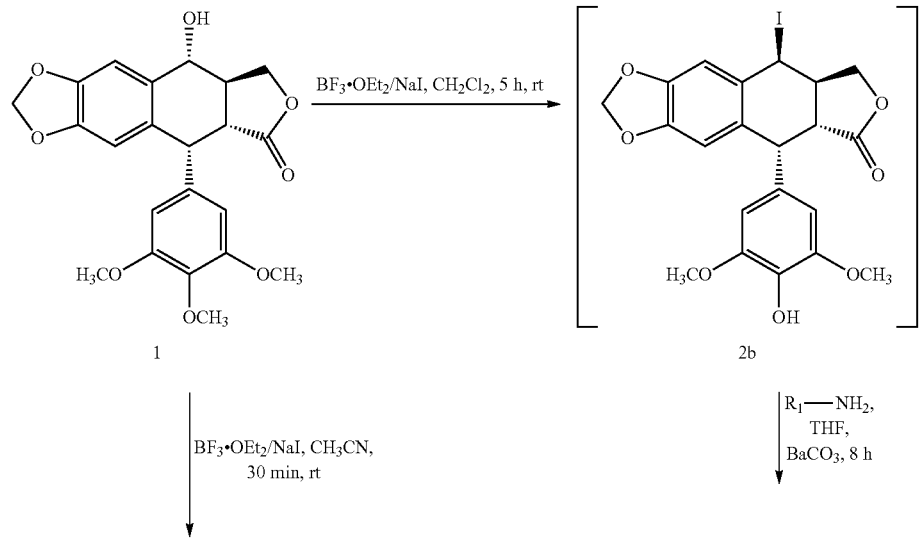

Some of the compounds of the present invention are given below:

a) 4β-(1"-Anthrylamino)-4-desoxypodophyllotoxin
b) 4'-O-Demethyl-4β-(1"-anthrylamino)-4-desoxypodophyllotoxin
c) 4β-(1"-Fluorenylamino)-4-desoxypodophyllotoxin
d) 4'-O-Demethyl-4β-(1"-fluorenylamino)-4-desoxypodophyllotoxin
e) 4β(1"-Pyrenylamino)-1-desoxypodophyllotoxin
f) 4'-O-Demethyl-4β-(1"-pyrenylamino)-4-desoxypodophyllotoxin
g) 4β-(6"-Chrycenylamino)-4-desoxypodophyllotoxin
h) 4'-O-Demethyl-4β-(1"-chrycenylamino)-4-desoxypodophyllotoxin
i) 4β-[4-(4"-(4"-Fluorobenzoyl)anilino]-4-desoxypodophyllotoxin
j) 4'-O-Demethyl-4β-[4"-(4"-fluorobenzoyl)anilino]-4-desoxypodophyllotoxin
k) 4β-(4"-{4"-[Di(2"-chloroethyl)amino]benzoyl}anilino)-4-desoxypodophyllotoxin
l) 4'-O-Demethyl-4β-(4"-{4"-[di(2"-chloroethyl)amino]benzoyl}anilino)-4-desoxy podophyllotoxin The following examples are given by the way of illustration and therefore should not be construed to limit the scope of the invention.

Example 1

4β-(1"-Anthrylamino)-4-desoxypodophyllotoxin (3a)

To a solution of podophyllotoxin (414 mg, 1 mmol) in dry acetonitrile (10 mL), sodium iodide (298 mg, 2 mmol) was added and stirred for 5 min to this stirred suspension $BF_3.Et_2$ (0.13 mL, 2 mmol) was added dropwise with at 0° C. and the stirring was continued for another 0.5 h at room temperature. This solution was then evaporated in vacuo and used for the next reaction without further purification. To the crude product, anhydrous barium carbonate (395 mg, 2 mmol) and 1-anthraceneamine (231 mg, 1.2 mmol) in 10 mL of dry THF under nitrogen was added and stirred for 8 h at room temperature. The reaction mixture was filtered, diluted with ethyl acetate and washed with water, 10% aqueous sodium thiosulphate solution, dried and purified via column chromatography using ethyl acetate/hexane mixture as eluent to get pure product in 90% yield.

m.p: 195-200° C. $[\alpha]^{25}_D$: −39.0 (c=1.0, $CHCl_3$)

$^1H$ NMR ($CDCl_3$): δ 3.1 (m, 1H), 3.3 (dd, 1H, J=13.6, 4.53 Hz), 3.78 (s, 6H), 3.8 (s, 3H), 3.97 (t, 1H, J=9.06 Hz), 4.43 (t, 1H, J=8 Hz), 4.67 (d, 2H, J=4.53 Hz), 4.95 (br, 1H), 5.97 (d, 2H, J=3.02 Hz), 6.33 (s, 2H), 6.43 (d, 1H, J=7.55 Hz), 6.6 (s, 1H), 6.8 (s, 1H), 7.28 (m, 1H), 7.43 (m, 3H), 7.94 (m, 2H), 8.24 (s, 1H), 8.35 (s, 1H).

$^{13}C$ NMR ($CDCl_3$): δ 38.78, 42.33, 43.75, 52.54, 56.41, 60.71, 69.0, 101.53, 108.75, 109.3, 110, 118.43, 118.81, 122.97, 125.44, 125.56, 125.85, 126.93, 127.80, 128.24, 130.68, 131.09, 131.82, 132.28, 132.54, 135.22, 142.43, 147.79, 148.40, 152.73, 174.64.

IR (KBr) cm$^{-1}$: 3409, 2903, 2834, 1774, 1586, 1503, 1481.
MS (FAB): 589 [M$^+$].

Example 2

4'-O-Demethyl-4β-(1"-anthrylamino)-4-desoxypodophyllotoxin (4a)

To a solution of podophyllotoxin (10) (414 mg, 1 mmol) in dry CH$_2$Cl$_2$ (10 mL), sodium iodide (298 mg, 2 mmol) was added and stirred for 5 min to this stirred suspension BF$_3$.OEt$_2$ (0.13 mL, 2 mmol) was added dropwise with at 0° C. and the stirring was continued for another 5 h at room temperature. Nitrogen was bubbled through the solution to drive of the excess hydrogen iodide. This solution was then evaporated in vacuo and used for the next reaction without further purification. To the above crude product, anhydrous barium carbonate (395 mg, 2 mmol) and 1-anthraceneamine (231 mg, 1.2 mmol) in 10 mL of dry THF under nitrogen was added and stirred for 8 h at room temperature. The reaction mixture was filtered, diluted with ethyl acetate and washed with water, 10% aqueous sodium thiosulphate solution, dried and purified via column chromatography using ethyl acetate/hexane mixture as eluent to get pure product in 65% yield.

m.p: 180-182° C. $[\alpha]^{25}_D$: −59.0 (c=1.0, CHCl$_3$)
$^1$H NMR (CDCl$_3$): δ 3.11 (m, 1H), 3.39 (dd, 1H, J=13.6, 4.53 Hz), 3.83 (s, 6H), 3.97 (t, 1H, J=9.1 Hz), 4.46 (t, 1H, J=8.31 Hz), 4.73 (m, 2H), 5.45 (br, 1H), 5.98 (d, 2H, J=1.51 Hz), 6.4 (s, 2H), 6.47 (d, 1H, J=7.55 Hz), 6.63 (s, 1H), 6.82 (s, 1H), 7.35 (m, 1H), 7.48°(m, 3H), 7.97 (m, 2H), 8.24 (s, 1H), 8.35 (s, 1H).
IR (KBr) cm$^{-1}$: 3416, 2924, 2852, 1773, 1576, 1481. MS (FAB): 575 [M$^+$].

Example 3

4β-(1"-Fluorenylamino)-4-desoxypodophyllotoxin (3b)

This compound was prepared according to the method described for 3a employing 1-fluorenylamine (220 mg, 1.2 mmol) and podophyllotoxin (414 mg, 1 mmol) to get pure product in 75% yield.

m.p: 209-212° C.; $[\alpha]^{25}_D$: −129.0 (c=1.0, CHCl$_3$)
$^1$H NMR (CDCl$_3$): δ 3.07 (m, 1H), 3.2 (dd, J=13.6, 4.53 Hz), 3.77 (s, 6H), 3.82 (s, 3H), 3.84 (s, 2H), 3.92 (br, 1H), 4.07 (t, 1H, J=9.06 Hz), 4.44 (t, 1H, J=8.31 Hz), 4.63 (d, 1H, J=4.53 Hz), 4.76 (m, 1H), 5.98 (d, 2H, J=3.02 Hz), 6.34 (s, 2H), 6.55 (s, 1H), 6.58 (dd, 1H, J=8.31, 2.27 Hz), 6.75 (m, 1H), 6.81 (s, 1H), 7.1-7.7 (m, 5H).
R (KBr) cm$^{-1}$: 3364, 2906, 2834, 1774, 1615, 1585, 1503, 1457.
MS (FAB): 577 [M$^+$].

Example 4

4'-40-Demethyl-4β-(1"-fluorenylamino)-4-desoxypodophyllotoxin (4b)

This compound was prepared, according to the method described for 4a employing 1-fluorenylamine (220 mg, 12 mmol) and podophyllotoxin (414 mg, 1 mmol) to get pure product in 63% yield.

m.p: 250-252° C. $[\alpha]^{25}_D$: −105.0 (c=1.0, CHCl$_3$)

$^1$H NMR (CDCl$_3$): δ 3.0-33 (m, 2H), 3.74 (s, 6H), 3.79 (s, 2H), 3.88 (m, 1H), 4.34 (t, 1H, J=7.81 Hz), 4.52 (d, 1H, J=5.21 Hz), 4.86 (m, 1H), 5.96 (s, 2H), 6.28 (s, 2H), 6.5 (s, 1H), 6.67 (m, 1H), 6.81 (s, 1H), 6.86 (m, 1H), 7.06-7.58 (m, 5H).
IR (KBr) cm$^{-1}$: 3349, 2925, 2854, 1758, 1610, 1515, 1458.
MS (FAB): 563 [M$^+$].

Example 5

4β-(1"-Pyrenylamino)-4-desoxypodophyllotoxin (3c)

This compound was prepared according to the method described for 3a employing 1-pyrenylamine (265 mg, 1.2 mmol) and podophyllotoxin (414 mg, 1 mmol) to get pure product in 67% yield.

m.p: 190-193° C.; $[\alpha]^{25}_D$: −122.0 (c=1.0, CHCl$_3$)
$^1$H NMR (CDCl$_3$): δ 3.19 (m, 1H), 3.34 (dd, 1H, J=14.16, 5.39 Hz), 3.82 (s, 6H), 3.84 (s, 3H), 4.02 (t, 1H, J=10.11 Hz), 4.5 (t, 1H, J=8.09 Hz), 4.7 (d, 1H, J=4.72 Hz), 4.86 (m, 1H), 5.11 (m, 1H), 6.01 (s, 2H), 6.37 (s, 2H), 6.62 (s, 1H), 6.83 (s, 1H), 7.1-8.1 (m, 9H).
IR (KBr) cm$^{-1}$: 3394, 2924, 1770, 1615, 1505, 1483.
MS (FAB): 617 [M$^+$].

Example 6

4'-O-Demethyl-4β-(1"-pyrenylamino)-4-desoxypodophyllotoxin (4c)

This compound was prepared according to the method described for 4a employing 1-pyrenylamine (265 mg, 1.2 mmol) and podophyllotoxin (414 mg, 1 mmol) to get pure product in 55% yield.

m.p: 148-153° C. $[\alpha]^{25}_D$: −76.0 (c=1.0, CHCl$_3$)
$^1$H NMR (CDCl$_3$): δ 3.13 (m, 1H), 3.29 (dd, 1H, J=13.6, 4.53 Hz), 3.83 (s, 6H), 3.98 (t, 1H, J=10.57 Hz), 4.44 (t, 1H, J=8.31 Hz), 4.55 (m, 1H), 4.66 (d, 1H, J=5.29 Hz), 5.07 (m, 1H), 5.34 (br, 1H), 5.97 (s, 2H), 6.35 (s, 2H), 6.59 (s, 1H), 6.8 (s, 1H), 7.18 (m, 1H), 7.9 (m, 8 Hz).
IR (KBr) cm$^{-1}$: 3381, 2920, 1775, 1603, 1510, 1483.
MS (FAB): 603 [M$^+$].

Example 7

4β-(6"-Chrycenylamino)-4-desoxypodophyllotoxin (3d)

This compound was prepared according to the method described for 3a employing 6-chrycenylamine (296 mg, 1.2 mmol) and podophyllotoxin (414 mg, 1 mmol) to get pure product in 71% yield.

m.p: 157-160° C. $[\alpha]^{25}_D$: −48.0 (c=1.0, CHCl$_3$)
$^1$H NMR (CDCl$_3$): δ 3.3 (m, 2H), 3.82 (s, 6H), 3.83 (s, 3H), 4.07 (t, 1H.; J=9.51 Hz), 4.61 (t, 2H, J=7.13 Hz), 4.72 (m, 2H), 5.21 (m, 1H), 6.0 (d, 2H, J=2.38 Hz), 6.38 (s, 2H), 6.57 (s, 1H), 6.86 (s, 1H), 7.4-9.0 (m, 11H).
IR (KBr) cm$^{-1}$: 3409, 2906, 1774, 1598, 1503, 1483.
MS (FAB): 643 [M$^+$].

Example 8

4'-O-Demethyl-4β-(6"-chrycenylamino)-4-desoxypodophyllotoxin (4d)

This compound was prepared according to the method described for 4a employing 6-chrycenylamine (296 mg, 1.2 mmol) and podophyllotoxin (414 mg, 1 mmol) to get pure product in 52% yield.

m.p: 158-160° C. $[\alpha]^{25}{}_D$: −39.0 (c=1.0, CHCl$_3$)
$^1$H NMR (CDCl$_3$): δ 3.34 (m, 2H), 3.84 (s, 6H), 4.08 (t, 1H, J=102 Hz), 4.59 (m, 1H), 4.74 (m, 2H), 5.21 (m, 1H), 5.98 (s, 2H,), 6.34 (s, 2H), 6.51 (s, 1H), 6.83 (s, 1H), 7.4-9.0 (m, 11H).
IR (KBr) cm$^{-1}$: 3394, 2923, 1768, 1615, 1503, 1482.
MS (FAB): 629 [M$^+$].

Example 9

4β-[4''-(4'''-Fluorobenzoyl)anilino]-4-desoaypodophyllotoxin (3e)

This compound was prepared according to the method described for 3a employing 4-amino-4'-fluorobenzophenone (258 mg, 1.2 mmol) and podophyllotoxin (414 mg, 1 mmol) to get pure product in 75% yield.
m.p: 106-110° C. $[\alpha]^{25}{}_D$: −106.0 (c=1.0, CHCl$_3$)
$^1$H NMR (CDCl$_3$): δ 3.02 (m, 2H), 3.75 (s, 6H), 3.78 (s, 3H), 4.4 (m, 2H), 4.58 (m, 1H), 4.8 (m, 1H), 5.95 and 5.98 (ABq, 2H, J=1.51 Hz), 6.25 (s, 2H), 6.55 (m, 3H), 6.78 (s, 1H), 7.12 (m, 2H), 7.72 (m, 4H).
IR (KBr) cm$^{-1}$: 3348, 2923, 1772, 1641, 1596, 1504, 1481.
MS (FAB): 611 [M$^+$].

Example 10

4'-O-Demethyl-4β-[4''-(4'''-fluorobenzoyl)anilino]-4-desoxypodophyllotoxin (4e)

This compound was prepared according to the method described for 4a employing 4-amino-4'-fluorobenzophenone (258 mg, 1.2 mmol) and podophyllotoxin (414 mg, 1 mmol) to get pure product in 65% yield.
m.p: 162-165° C. $[\alpha]^{25}{}_D$: −129.0 (c=1.0, CHCl$_3$)
$^1$H NMR (CDCl$_3$): δ 3.02 (m, 2H), 3.79 (s, 6H), 4.36 (m, 1H), 4.52 (m, 2H), 4.79 (m, 1H), 5.35 (br, 1H), 5.95 and 5.98 (ABq, 2H, J=1.51 Hz), 6.28 (s, 2H), 6.51 (s, 1H), 6.57 (d, 2H, J=8.69 Hz), 6.76 (s, 1H), 7.13 (m, 2H), 7.68-7.79 (m, 4H).
IR (KBr) cm$^{-1}$: 3402, 2924, 1775, 1610, 1503, 1481.
MS (FAB): 597 [M$^+$].

Example 11

4β-(4''-{4'''-[Di(2''''-chloroethyl)amino]benzoyl}anilino)-4-desoxypodophyllotoxin (3f)

This compound was prepared according to the method described for 3a employing 4-amino-4'-[di(2-chloroethyl)amino]benzophenone (404 mg, 1.2 mmol) and podophyllotoxin (414 mg, 1 mmol) to get pure product in 65% yield.
m.p: 186-190° C. $[\alpha]^{25}{}_D$: −110.0 (c=1.0, CHCl$_3$)
$^1$H NMR (CDCl$_3$): δ 3.13 (m, 2H), 3.64-3.91 (m, 17H), 3.99 (m, 1H), 4.26-4.48 (m, 2H), 4.63 (m, 1H), 4.81 (m, 1H), 5.99 (d, 2H, J=6.8 Hz), 6.33 (s, 2H), 6.55 (s, 1H), 6.57-6.74 (m, 4H), 6.8 (s, 1H), 7.66-7.8 (m, 4H).
IR (KBr) cm$^{-1}$: 3380, 2924, 2854, 1773, 1727, 1596, 1507, 1480.
MS (FAB): 733 [M$^+$].

Example 12

4'-O-Demethyl-4β-(4''-{4'''-[di(2''''-chloroethyl)amino]benzoyl}anilino)-4-desoxy podophyllotoxin (4f)

This compound was prepared according to the method described for 4a employing 4-amino-4'-[di(2-chloroethyl)amino]benzophenone (404 mg, 1.2 mmol) and podophyllotoxin (414 mg, 1 mmol) to get pure product in 51% yield.
m.p: 173-175° C. $[\alpha]^{25}{}_D$: −124:0 (c=1.0, CHCl$_3$)
$^1$H NMR (CDCl$_3$): δ 3.12 (m, 2H), 3.65-3.88 (m, 14H), 3.99 (t, 1H, J=10.57 Hz), 4.48 (m, 2H), 4.62 (d, 1H, J=4.53 Hz), 4.82 (m, 1H), 5.34 (br, 1H), 5.98 (d, 2H, J=6.8 Hz), 6.33 (s, 2H), 6.55 (s, 1H), 6.57-6.74 (m, 4H), 6.8 (s, 1H), 7.66-7.8 (m, 4H).
IR (KBr) cm$^{-1}$: 3395, 2920, 1772, 1598, 1507, 1481.
MS (FAB): 719 [M$^+$].

Biological Activity:
In Vitro Evaluation of Cytotoxic Activity

Compounds 3a-f and 4a-f have been evaluated for their in vitro cytotoxicity in selected human cancer cell lines i.e., Liver (HEP-2), Neuroblastoma (IMR-32), Breast (MCF-7), CNS (SK-N-SH) and Colon (Colo-205, SW-620) origin by employing the sulforhodamine B (SRB) assay method (Skehn, P.; Storeng, R.; Scudiero, A.; Monks, J.; McMohan, D.; Vistica, D.; Jonathan, T. W.; Bokesch, H.; Kenney, S.; Boyd M. R. *J. Natl. Cancer Inst.* 1990, 82, 1107). The results (µM/ml) are summarized with standard drug Adriamycin in Table-1. All the new compounds were significantly cytotoxic towards the liver, CNS and colan cancer cell lines compared, to the standard drug tested, with the fixed concentration of the drug (10 µM).

TABLE 1

In Vitrocytotoxicity data of compounds 3a-f and 4a-f

| Compound | Concentration (µM/mL) | Growth Inhibition(%) | | | | | |
|---|---|---|---|---|---|---|---|
| | | Liver HEP-2 | Neuroblastma IMR-32 | Breast MCF-7 | CNS SK-N-SH | Colon Colo-205 | SW-620 |
| 3a | 1 × 10$^{-5}$ | 46 | 16 | 5 | 65 | 55 | 25 |
| 4a | 1 × 10$^{-5}$ | 58 | 0 | 0 | 38 | 39 | 22 |
| 3b | 1 × 10$^{-5}$ | 77 | 0 | 4 | 44 | 49 | 11 |
| 4b | 1 × 10$^{-5}$ | 0 | 0 | 39 | 50 | 55 | 15 |
| 3c | 1 × 10$^{-5}$ | 66 | 0 | 0 | 59 | 64 | 29 |
| 4c | 1 × 10$^{-5}$ | 39 | 0 | 0 | 40 | 40 | 7 |
| 3d | 1 × 10$^{-5}$ | 66 | 1 | 0 | 73 | 51 | 14 |
| 4d | 1 × 10$^{-5}$ | 76 | 0 | 0 | 58 | 58 | 17 |
| 3e | 1 × 10$^{-5}$ | 0 | 0 | 30 | 34 | 68 | 10 |
| 4e | 1 × 10$^{-5}$ | 51 | 11 | 39 | 91 | 77 | 42 |
| 3f | 1 × 10$^{-5}$ | 45 | 0 | 40 | 83 | 74 | 15 |
| ADR | 1 × 10$^{-6}$ | 23 | 0 | 23 | 36 | 18 | 21 |

ADR = Adriamycin is the control drug

Apart from this, some of these analogues were evaluated for Topoisomerase-I relaxation, Topoisomerase-II inhibition, DNA laddering assay and DNA cell cycle analysis. Compounds 3c, 4c, 3d and 4d were analyzed for topoisomerase-I assay at 100 µM (FIG. 2) only compound 3d was found active and rest were not active. Compounds 3d, 4d and 4c were analyzed for topoisomerase inhibition assay. None of the compounds are active, however compound 3d shows better activity than others (FIG. 3).

Compound 3d evaluated for DNA laddering assay. This compound at 0.5, 1, 5, and 10 µM concentration induced DNA fragmentation in leukemia (MOLT-4) cells after 24 hr incubation (FIG. 4). Further this compound (3d) evaluated for DNA cell cycle analysis at 0.5, 1, 5, and 10 µM concentrations by treated with Lukemia (HL-60) cells indicated that it blocks the G1 Phase of cell cycle and there was increase in sub G1 cell population indicates apoptosis (FIG. 5).

Procedure of the SRB-Assay

Single cell suspension of the tumor cells grown in tissue culture were made, cells counted and cell count adjusted to $1 \times 10^5$ to $5 \times 10^5$ Ninetysix (96) well plates were seeded with this cell suspension, each well receiving 100 µl of it. The plate was then be incubated at 37° C. temperature in $CO_2$ incubator for 24 hours. Drugs were added at appropriate concentrations after 24-hour, incubation followed by further incubation for 48 hours. Experiment was terminated by gently layering the cells in the wells with 30% TCA and plates were kept in refrigerator for 1 hour following which they were washed thoroughly with tap water, dried attained with 0.4% SRB in 1% acetic aid and finally, the bound SRB eluted with 10 mM tris. Absorbance was read at 540 nm, in the microtitre-plate reader. Optical density of drug-treated cells was compared with that of control cells and cell inhibition was calculated as percent values. Each compound was tested at 10, 20, 40 and 80 µg/ml in triplicate on human malignant cell lines.

Topoisomerase-I Relaxation Assay

Reaction was assembled in micro centrifuge tube that contains super coiled DNA 250 ng/µl & Topoisomerase-I (4 units) in assay buffer (10 mM Tris-HCl, pH 7.9, 0.15 M NaCl, 0.1% BSA, and 5.0 mM (beta)-mercaptoethanol). In each reaction 2 µl sample was added then volume was made up to 20 µl with water and then incubated at 37° C. Reaction was terminated by addition of 2 µl of 10% SDS. Each sample tube was treated with proteinase K and extracted once with chloroform: isoamyl alcohol. Products were resolved by 0.8% agarose gel electrophoresis in TAE buffer (40 mM tris-acetate, pH 8.0, and 1 mM EDTA) and stained with 0.5 µg/ml ethedium bromide (EtBr). Results are shown in FIG. 2.

DNA Topoisomerase-II Inhibition Assay

Reaction was assembled in micro centrifuge tube that contains super coiled DNA 250 ng/µl & Topoisomerase-I (4 units) in assay buffer (A 0.1 volume and B 1 volume)). In each reaction 2 µl sample was added then volume was made up to 20 µl with water and then incubated at 37° C. Reaction was terminated by addition of 2 µl of 10% SDS. Each sample tube was treated with proteinase K and extracted once with chloroform: isoamyl alcohol. Products were resolved by 0.8% agarose gel electrophoresis in TAE buffer (40 mM tris-acetate, pH 8.0, and 1 mM. EDTA) and stained with 0.5 µg/ml, ethedium bromide (EtBr). Results are shown in FIG. 3.

DNA Gel Electophoresis

DNA fragmentation was determined by electrophoresis of extracted genomic DNA form leukemia cell (MOLT4). Briefly, exponentially growing cells ($2 \times 10^6$ cells/mL) in 6 well plate were treated with compound 3d in 0.5, 1, 5 and 10 µM concentrations for 24 hrs. Cells were harvested, washed with PBS, pellets were dissolved in lyris buffer (10 mM EDTA, 50 mM Tris pH 8.0, 0.5% w/v SDS and proteinase K (0.5 mg/mL) and incubated at 50° C. for 1 hr. Finally the DNA obtained was heated rapidly to 70° C., supplemented with loading dye and immediately resolved on to 1.5% agarose gel at 50 V for 2-3 hrs (FIG. 4).

Flow-Cytometric Analysis of Phase Distribution of Nuclear DNA

Effect of compound 3d on DNA content by cell cycle phase distribution was assessed using HL-60 cells by incubating the HL-60 cells ($1 \times 10^6$) 1 ml phosphate buffer saline were treated with 3d (0.5, 1, 5, 10 µM) for 24 hr. The cells were then washed twice with ice-cold PBS, harvested, fixed with ice cold PBS in 70% ethanol, and stored at −20° C. for 30 minutes. After Fixation, these cells were incubated with RNase A (0.1 mg/ml) at 37° C. for 30 min, stained with propidium iodide (50 µg/ml) for 30 min on ice in dark, and then measured for DNA content using BD-LSR flow cytometer (Becton Dickinson, USA) equipped with electronic doublet discrimination capability using blue (488 nm) excitation from orgon laser. Data were collected in list mode on 10,000 events for FL2-A vs. FL2-W (FIG. 5).

In conclusion, the main advantages of the present inventions are that these new 4β-polyarylamine analogues of podophyllotoxin have exhibited promising in vitro cytotoxic activity. Further, these compounds have been prepared from podophyllotoxin upon reaction with $BF_3.OEt_2$/NaI followed by the addition of corresponding polyaryl amines in the presence of $BaCO_3$ at room temperature to provide the 4β-polyarylamino podophyllotoxin analogues in very good yields and in almost stereoselective manner.

We claim:

1. A podophyllotoxin congener of general formula A

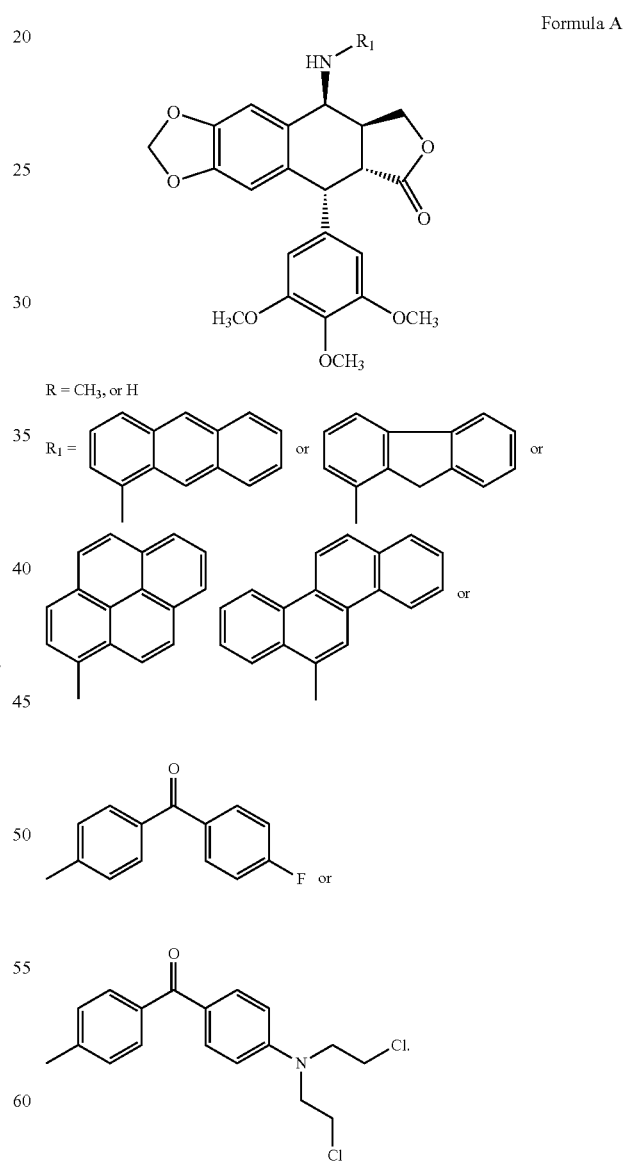

2. The podophyllotoxin congener of formula A as claimed in claim 1, represented by the compounds of formula 3a-f or formula 4a-f

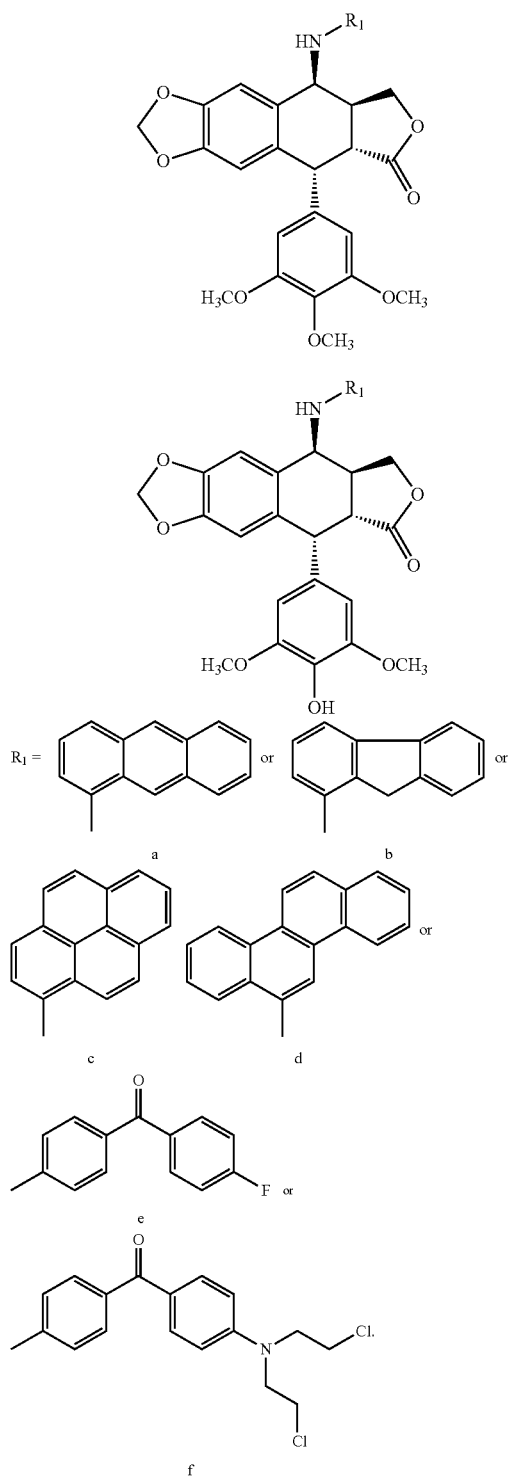

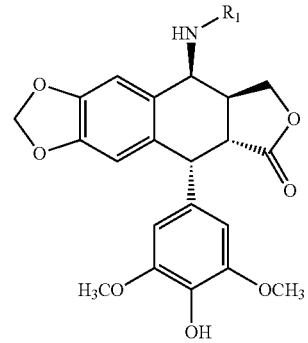

4β-(4"-{4"-[Di(2"-chloroethyl)amino]benzoyl}anilino)-4-desoxypodophyllotoxin (3f);

4'-O-Demethyl-4β-(1"-anthrylamino)-4-desoxypodophyllotoxin (4a);

4'-O-Demethyl-4β-(1"-fluorenylamino)-4-desoxypodophyllotoxin (4b);

4'-O-Demethyl-4β-(1"-pyrenylamino)-4-desoxypodophyllotoxin (4c);

4'-O-Demethyl-4β-(1"-chrycenylamino)-4-desoxypodophyllotoxin (4d);

4'-O-Demethyl-4β-[4"-(4"-fluorobenzoyl)anilino]-4-desoxypodophyllotoxin (4e) and 4'-O-Demethyl-4β-(4"-{4"-[di(2"-chloroethyl)amino]benzoyl} anilino)-4-desoxy podophyllotoxin (4f).

4. A process for the preparation of a podophyllotoxin congener of general formula A 3. The podophyllotoxin congener as claimed in claim 1 is represented by a compound selected from the group consisting of:

4β-(1"-Anthrylamino)-4-desoxypodophyllotoxin (3a);
4β-(1"-Fluorenylamino)-4-desoxypodophyllotoxin (3b);
4β-(1"-Pyrenylamino)-4-desoxypodophyllotoxin (3c);
4β-(6"-Chrycenylamino)-4-desoxypodophyllotoxin (3d);
4β-[4"-(4"-Fluorobenzoyl)anilino]-4-desoxypodophyllotoxin (3e);

wherein the process comprises the steps of:
a) reacting podophyllotoxin of formula 1

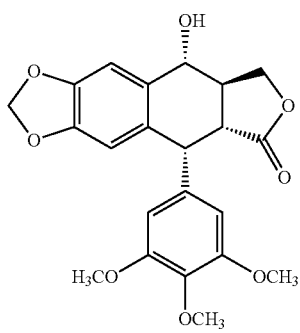

1 with sodium iodide in dry acetonitrile, while stirring, followed by adding drop wise BF$_3$OEt$_2$ at a temperature of 0-1° C. and continuing the stirring for a period of 0.3-0.6 hrs, at a temperature of 20-30° C., followed by evaporation in vacuo to obtain a compound of formula 2a,

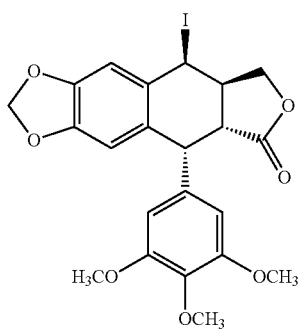

2a or
b) reacting the podophyllotoxin of formula 1 with sodium iodide in dry dichloromethane, while stirring, followed by adding drop wise BF$_3$OEt$_2$ at a temperature of 0-1° C. and continuing the stirring for a period of 5-6 hrs, at a temperature of 20-30° C., followed by evaporation in vacuo to obtain a compound of formula 2b,

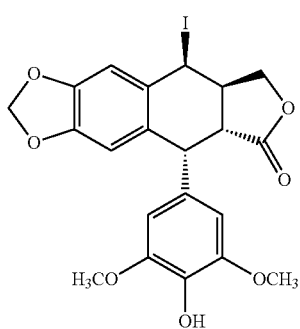

2b c) reacting the compound of formula 2a or 2b with anhydrous barium carbonate and the reagent selected from the group consisting of 1-anthraceneamine, 1-fluorenylamine, 4β-(1″-pyrenylamino)-4-deoxypodophyllotoxin, 1-pyrenylamine, 6-chrycenylamine, 4-amino-4′-fluorobenzophenone and 4-amino-4′-[di(2-chloroethyl)amino]benzophenone in dry tetrahydrofuran (THF), under nitrogen and stirring for a period of 7-9 hrs. at a temperature of 20-30° C., followed by filtration, washing with water and drying to obtain a compound of formula 3a-f or formula 4a-f.

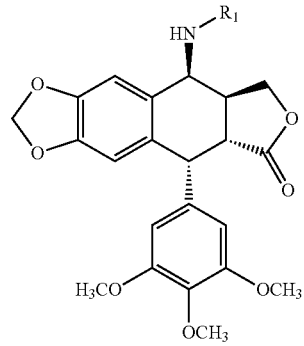

3a-f

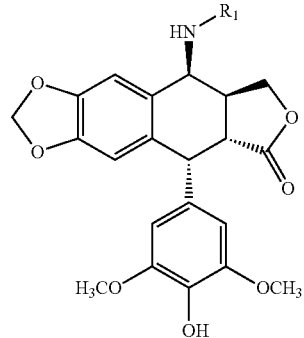

4a-f

R$_1$ =

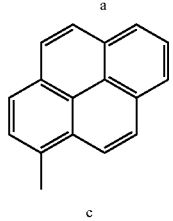

a or

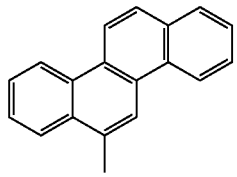

b or c or d or

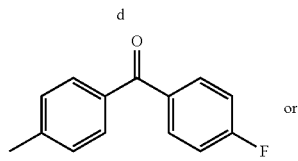

e or

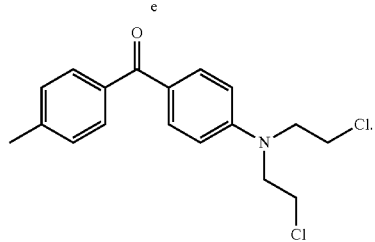

f

5. The process of claim 4, wherein the compound of formula 3a-f or formula 4-f is selected from the group consisting of:

4β-(1"-Anthrylamino)-4-desoxypodophyllotoxin (3a);
4β-(1"-Fluorenylamino)-4-desoxypodophyllotoxin (3b);
4β-(1"-Pyrenylamino)-4-desoxypodophyllotoxin (3c);
4β-(6"-Chrycenylamino)-4-desoxypodophyllotoxin (3d);
4β-[4"-(4"-Fluorobenzoyl)anilino]-4-desoxypodophyllotoxin (3e);
4β{4"-[Di(2"-chloroethyl)amino]benzoyl}anilino)-4-desoxypodophyllotoxin (3f);
4'-O-Demethyl-4β-(1"-anthrylamino)-4-desoxypodophyllotoxin (4a);
4'-O-Demethyl-4β-(1"-fluorenylamino)-4-desoxypodophyllotoxin (4b);
4'-O-Demethyl-4β-(1"-pyrenylamino)-4-desoxypodophyllotoxin (4c);
4'-O-Demethyl-4β-(1"-chrycenylamino)-4-desoxypodophyllotoxin (4d);
4'-O-Demethyl-4β-[4"-(4"-fluorobenzoyl)anilino]-4-desoxypodophyllotoxin (4e)
and
4'-O-Demethyl-4β-(4"-{"-[di(2"-chloroethyl)amino]benzoyl}anilio)-4-desoxypodophyllotoxin (4f).

6. The process of claim 4, wherein the podophyllotoxin congener is an antitumour antibiotic.

\* \* \* \* \*